US009869656B2

(12) United States Patent
Uemura (10) Patent No.: US 9,869,656 B2
(45) Date of Patent: Jan. 16, 2018

(54) IMPEDANCE DETECTOR FOR OXYGEN CONCENTRATION SENSOR ELEMENT (71) Applicant: DENSO CORPORATION, Kariya, Aichi-pref. (JP)

(72) Inventor: Shinya Uemura, Obu (JP)

(73) Assignee: DENSO CORPORATION, Kariya (JP)

( * ) Notice: Subject to any disclaimer, the term of this patent is extended or adjusted under 35 U.S.C. 154(b) by 319 days.

(21) Appl. No.: 14/669,586

(22) Filed: Mar. 26, 2015

(65) Prior Publication Data

US 2015/0293044 A1    Oct. 15, 2015

(30) Foreign Application Priority Data

Apr. 11, 2014    (JP) .................................. 2014-82083

(51) Int. Cl.
*G01R 27/08*    (2006.01)
*G01N 27/406*    (2006.01)
(Continued)

(52) U.S. Cl.
CPC ......... *G01N 27/4065* (2013.01); *G01N 27/02* (2013.01); *G01N 27/409* (2013.01); *G01N 27/419* (2013.01); *G01N 27/028* (2013.01)

(58) Field of Classification Search
CPC .... G01N 27/02; G01N 27/028; G01N 27/409; G01N 27/4065; G01N 27/419
(Continued)

(56) References Cited

U.S. PATENT DOCUMENTS 5,547,552 A * 8/1996 Hasegawa ........... F02D 41/1494
204/401
5,781,878 A * 7/1998 Mizoguchi .......... F02D 41/1495
701/109
(Continued)

FOREIGN PATENT DOCUMENTS

JP    H11-230931 A    8/1999
JP    2000-81414 A    3/2000
(Continued)

OTHER PUBLICATIONS

Information Offer Form mailed Jan. 8, 2016 in the corresponding JP application No. 2014-82083.

*Primary Examiner* — Patrick Assouad
*Assistant Examiner* — Sean Curtis
(74) *Attorney, Agent, or Firm* — Posz Law Group, PLC (57) ABSTRACT In an impedance detector, a current application portion applies a first current and a second current, directions of which are opposite to each other, to an element of an oxygen concentration sensor. A detection portion detects a difference between a current application prior voltage and a current application subsequent voltage. The current application prior voltage is a voltage between both of ends of the element before being applied with the first current, and the current application subsequent voltage is a voltage between both of the ends of the element when being applied with the first current. An impedance calculation portion calculates an impedance of the element based on the difference detected by the detection portion and a value of the first current. The current application portion is configured to change a current application time to apply the first current and the second current according to a command provided thereto.

11 Claims, 5 Drawing Sheets

(51) Int. Cl.
  *G01N 27/02* (2006.01)
  *G01N 27/419* (2006.01)
  *G01N 27/409* (2006.01)

(58) Field of Classification Search
  USPC .............. 324/647, 649, 691, 693, 705, 713;
  204/406, 424; 73/1.06, 23.32,
  73/114.72–114.73; 205/785
  See application file for complete search history.

(56) References Cited

U.S. PATENT DOCUMENTS

| | | | | |
|---|---|---|---|---|
| 5,993,641 A * | 11/1999 | Okazaki | ............. | F02D 41/1456 204/424 |
| 6,084,418 A * | 7/2000 | Takami | ............... | F02D 41/1494 204/424 |
| 6,094,975 A * | 8/2000 | Hasegawa | ........... | F02D 41/1494 123/688 |
| 6,120,677 A * | 9/2000 | Yamada | ............... | F02D 41/1494 204/408 |
| 6,205,989 B1 * | 3/2001 | Aoki | .................... | F02D 41/1455 123/688 |
| 6,242,928 B1 * | 6/2001 | Honda | ................ | G01N 27/4067 324/71.1 |
| 6,258,232 B1 * | 7/2001 | Hasegawa | ........... | F02D 41/1494 204/424 |
| 6,304,813 B1 * | 10/2001 | Ikeda | .................. | F02D 41/1494 123/697 |
| 6,347,544 B1 * | 2/2002 | Hada | ................... | F02D 41/1495 123/693 |
| 6,397,659 B1 * | 6/2002 | Mizoguchi | ........... | G01N 27/407 73/23.2 |
| 6,468,478 B1 * | 10/2002 | Honda | ................ | G01N 27/4175 324/717 |
| 6,831,471 B2 * | 12/2004 | Gertiser | .............. | F02D 41/1441 324/609 |
| 7,043,957 B2 * | 5/2006 | Hattori | ............... | G01N 27/4175 73/1.06 |
| 7,393,441 B2 * | 7/2008 | Tashiro | ............... | F02D 41/1454 204/406 |
| 7,481,913 B2 * | 1/2009 | Kawase | ............. | G01N 27/4065 204/406 |
| 7,955,494 B2 * | 6/2011 | Kawase | ............. | G01N 27/4065 204/406 |
| 8,623,186 B2 * | 1/2014 | Kato | .................. | G01N 27/4067 204/424 |
| 9,523,654 B2 * | 12/2016 | Uemura | .............. | F02D 41/1454 |
| 9,529,019 B2 * | 12/2016 | Uemura | ................. | G01R 17/00 |
| 2001/0000956 A1 * | 5/2001 | Honda | ............... | G01N 27/4067 338/34 |
| 2004/0099041 A1 * | 5/2004 | Hattori | ............... | H01N 27/4175 43/1.06 |
| 2005/0000810 A1 * | 1/2005 | Tashiro | ............... | F02D 41/1454 204/424 |
| 2005/0029098 A1 * | 2/2005 | Aoki | ................... | G01N 27/4065 204/406 |
| 2006/0011476 A1 * | 1/2006 | Hada | .................. | G01N 27/4065 204/406 |
| 2006/0049048 A1 * | 3/2006 | Kondo | .............. | G01N 27/4074 204/425 |
| 2007/0034531 A1 * | 2/2007 | Kato | ..................... | G01N 27/419 205/785.5 |
| 2007/0045112 A1 * | 3/2007 | Tashiro | ................. | F02D 41/123 204/401 |
| 2008/0277281 A1 * | 11/2008 | Hiraiwa | .............. | G01N 27/4067 204/406 |
| 2009/0084677 A1 * | 4/2009 | Kawase | .............. | G01N 27/4065 204/402 |
| 2010/0122568 A1 * | 5/2010 | Inoue | .................. | G01N 27/4065 73/31.05 |
| 2014/0278013 A1 * | 9/2014 | Gibson | .................. | G01R 27/02 701/108 |
| 2015/0219590 A1 * | 8/2015 | Uemura | .............. | F02D 41/1454 73/23.32 |
| 2015/0219694 A1 * | 8/2015 | Uemura | ................. | G01R 17/00 324/649 |
| 2015/0293044 A1 * | 10/2015 | Uemura | ............... | G01N 27/4065 324/693 |
| 2015/0323493 A1 * | 11/2015 | Uemura | ................. | F02D 41/28 204/406 |
| 2016/0123922 A1 * | 5/2016 | Akimoto | ............ | G01N 27/4175 204/401 |
| 2017/0067798 A1 * | 3/2017 | Uemura | ............. | G01N 27/4065 |

FOREIGN PATENT DOCUMENTS

| | | | |
|---|---|---|---|
| JP | 2000-329730 A | | 11/2000 |
| JP | 2002-257783 A | | 9/2002 |
| JP | 2002257783 A | † | 9/2002 |
| JP | 2004-177178 A | | 6/2004 |
| JP | 2005-227013 A | | 8/2005 |

\* cited by examiner
† cited by third party

IMPEDANCE DETECTOR FOR OXYGEN CONCENTRATION SENSOR ELEMENT

CROSS REFERENCE TO RELATED APPLICATION

This application is based on Japanese Patent Application No. 2014-82083 filed on Apr. 11, 2014, the disclosure of which is incorporated herein by reference

TECHNICAL FIELD

The present disclosure relates to an impedance detector for detecting an impedance of an element of an oxygen concentration sensor.

BACKGROUND

For example, JP H10-48180 A, which corresponds to U.S. Pat. No. 6,120,677, describes a technology for detecting the impedance of an element (element impedance) of an oxygen concentration sensor that is used for controlling an air fuel ratio of an internal combustion engine.

In the technology of JP H10-48180 A, a constant current for measuring an impedance, that is, for measuring a resistance value is applied to a cell as the element only for a fixed period of time. A difference between a both-end voltage of the element before being applied with the constant current and a both-end voltage of the element when being applied with the constant current is detected as a value that is correlated with the impedance of the element. The difference corresponds to the amount of change of the both-end voltage due to application of the constant current.

In the technology of JP H10-48180 A, after the constant current for measuring the resistance value is applied to the cell, a constant current having an opposite polarity is applied to the cell only for the same fixed period of time so as to shorten the time to return the cell to a normal state for detecting the air fuel ratio.

SUMMARY

The optimum value of the period of time to apply the constant current is different depending on electrical characteristics of the cell (element) to which the constant current is applied as an object to detect the impedance, that is, depending on the type of the oxygen concentration sensor. This is because a period from the time the application of the constant current to the cell begins to the time the both-end voltage of the cell reaches a value according to the impedance is different depending on the electrostatic capacity and the resistance value of the cell.

Therefore, in the case where the period of time to apply the constant current is fixed, when the characteristic of the oxygen concentration sensor is changed, such as when the oxygen concentration sensor is changed to one having a different parts number or when the characteristic is changed without changing the parts number, the period of time to apply the constant current may be too short or too long. If the period of time to apply the constant current is too short, the application of the constant current ends before the both-end voltage of the cell reaches the value corresponding to the impedance. As a result, the change of the both-end voltage of the cell due to the application of the constant current, that is, the impedance of the cell cannot be accurately detected. If the period of time to apply the constant current is too long, a period in which the air fuel ratio cannot be detected becomes long, and thus it is not preferable.

It is an object of the present disclosure to provide an impedance detector for an element of an oxygen concentration sensor, which is capable of optimizing a detection operation of the impedance according to an oxygen concentration sensor employed.

According to an aspect of the present disclosure, an impedance detector is for detecting an impedance of an element of an oxygen concentration sensor. The impedance detector includes a current application portion, a detection portion, and an impedance calculation portion. The current application portion applies a first current and a second current, directions of which are opposite to each other, to the element of the oxygen concentration sensor in order. The detection portion detects a difference between a current application prior voltage and a current application subsequent voltage. The current application prior voltage is a voltage between both of ends of the element before being applied with the first current, and the current application subsequent voltage is a voltage between both of the ends of the element when being applied with the first current. The impedance calculation portion calculates an impedance of the element based on the difference detected by the detection portion and the value of the first current. The current application portion is configured to change a current application time that is a period of time to apply the first current and the second current according to a command provided to the current application portion.

In the above structure, the impedance detector can change the current application time to a suitable value according to the oxygen concentration sensor employed. As a result, the detection operation of the impedance can be optimized.

BRIEF DESCRIPTION OF THE DRAWINGS

The above and other objects, features and advantages of the present disclosure will become more apparent from the following detailed description made with reference to the accompanying drawings, in which like parts are designated by like reference numbers and in which.

DETAILED DESCRIPTION

Embodiments of the present disclosure will be hereinafter described.

In the embodiments, a control device is employed to a fuel injection control system that performs a feedback control of an air fuel ratio of an internal combustion engine of a vehicle, that is, that controls the amount of fuel injection so as to have a target air fuel ratio.

Hereinafter, description will be made mainly about structure and processing for detecting an impedance of an element of an oxygen concentration sensor that is used for detecting an actual air fuel ratio in the fuel injection control system.

First Embodiment

Figure 1:
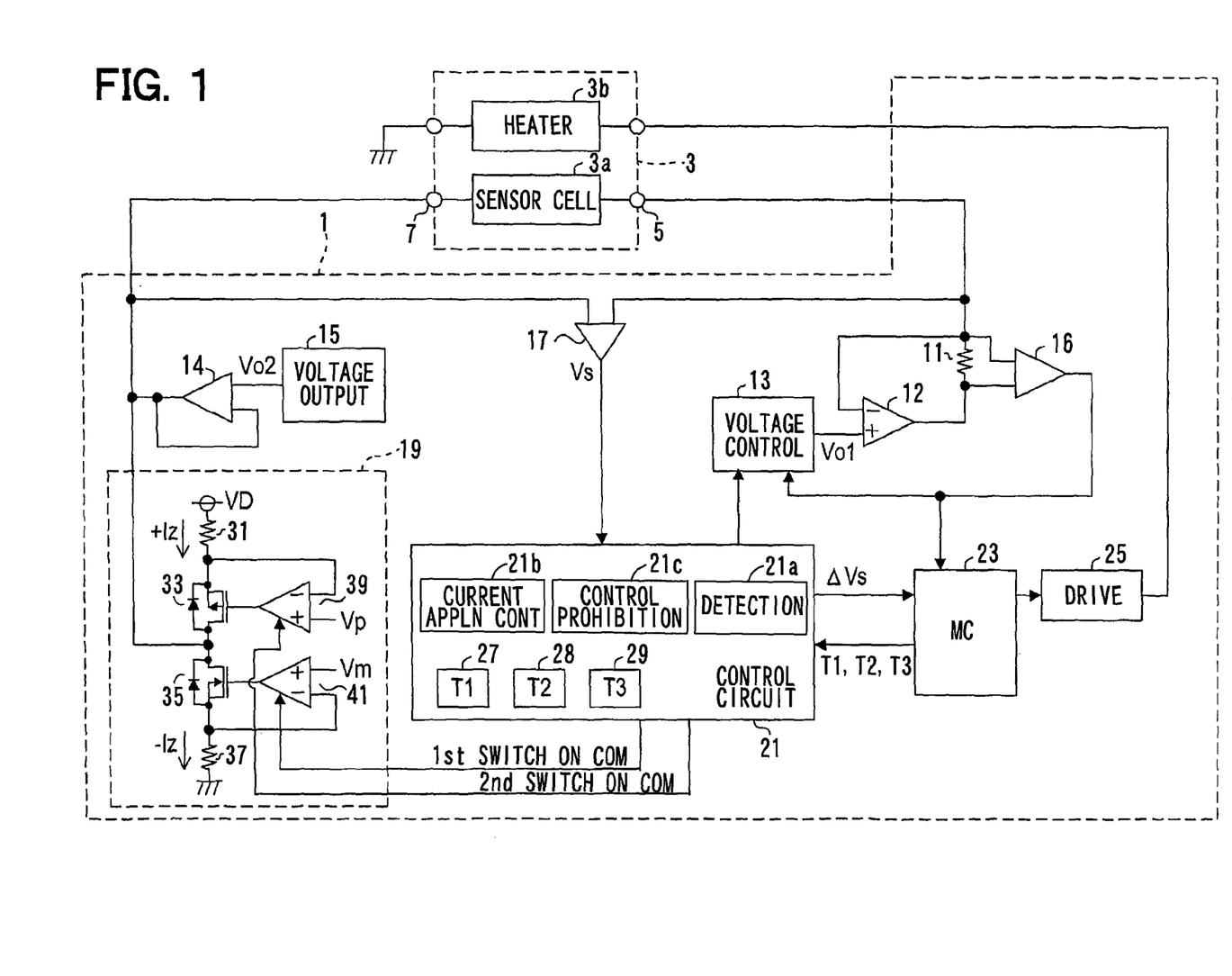
FIG. 1 is a schematic block diagram illustrating a structure of a control device for an impedance detector according to a first embodiment of the present disclosure.

As shown in FIG. 1, an air fuel ratio sensor 3 for detecting an air fuel ratio is connected to a control device 1 of a first embodiment.

The air fuel ratio sensor 3 is a one-cell type air fuel ratio sensor, such as a limiting current-type one cell air fuel ratio sensor. The air fuel ratio sensor 3 is installed in an exhaust passage of the engine of the vehicle. The air fuel ratio sensor 3 includes a sensor cell 3a and a heater 3b. The sensor cell 3a generates a limiting current according to an air fuel ratio of an exhaust gas in a state of being applied with voltage. The heater 3b is provided to heat the sensor cell 3a. The limiting current generated by the sensor cell 3a is a sensor current according to the air fuel ratio detected by the air fuel ratio sensor 3. In this example, the sensor cell 3a corresponds to an element that is an object to detect impedance.

The sensor cell 3a has a first terminal 5 and a second terminal 7. For example, the first terminal 5 is a positive-side terminal, and the second terminal 7 is a negative-side terminal. The control device 1 includes a resistor 11 for detecting the sensor current. A first end of the resistor 11 is connected to the first terminal 5 of the sensor cell 3a. The control device 1 includes an operational amplifier 12 and a voltage control part 13 for applying a voltage to the first terminal of the sensor cell 3a and for allowing the sensor current to flow in the sensor cell 3a through the resistor 11. The control device 1 further includes a buffer circuit 14 and a voltage output part 15 for applying a voltage to the second terminal 7 of the sensor cell 3a. The control device 1 further includes an amplifier circuit 16 that amplifies and outputs a voltage between both ends of the resistor 11 (both-end voltage).

An output terminal of the operational amplifier 12 is connected to a second end of the resistor 11, which is opposite to the first end connected to the first terminal 5 of the sensor cell 3a. An inverted input terminal (negative-side terminal) of the operational amplifier 12 is connected to the first terminal 5 of the sensor cell 3a. A non-inverted input terminal (positive-side terminal) of the operational amplifier 12 receives an output voltage Vo1 outputted from the voltage control part 13. Therefore, a voltage of the output terminal of the operational amplifier 12 changes so that the voltage of the first terminal 5 and the output voltage Vo1 of the voltage control part 13 are equal to each other.

The buffer circuit 14 is provided by an operational amplifier. The buffer circuit 14 outputs a voltage having the same voltage value as that of an output voltage Vo2 outputted from the voltage output part 15 to the second terminal 7 of the sensor cell 3a.

Therefore, the sensor cell 3a is applied with a difference voltage (Vo1−Vo2) between the output voltage Vo1 of the voltage control part 13 and the output voltage Vo2 of the voltage output part 15. That is, the difference voltage is an application voltage to the sensor cell 3a for detecting the air fuel ratio. For example, when the output voltage Vo1 is 2.9 V and the output voltage V2 is 2.5 V, the sensor cells 3a is applied with the voltage of 0.4 V.

The amplifier circuit 16 outputs a voltage proportional to the sensor current. That is, the voltage outputted from the amplifier circuit 16 corresponds to a detection signal of the sensor current.

The voltage control part 13 adjusts the output voltage Vo1 according to the output voltage of the amplifier circuit 16, that is, according to the sensor current, thereby to adjust the application voltage to the sensor cell 3a. Specifically, the voltage control part 13 adjusts the application voltage to the sensor cell 3a according to the sensor current, for example, to a median value of a range where the air fuel ratio correctly corresponds to the sensor current, that is, a range where the air fuel ratio and the sensor current correspond uniquely. For example, the application voltage is increased as the sensor current is increased with the increase in air fuel ratio.

The control device 1 further includes an amplifier circuit 17, a current application circuit 19, a control circuit 21, a microcomputer 23, and a drive circuit 25. The amplifier circuit 17 amplifies and outputs the both-end voltage Vs of the sensor cell 3a (hereinafter referred to as a sensor-across voltage Vs). The current application circuit 19 applies a current for detecting an impedance Z of the sensor cell 3a to the sensor cell 3a. The control circuit 21 performs control for detecting the impedance Z. The drive circuit 25 turns on a heater 3b according to a command provided from the microcomputer 23. A magnification of the amplifier circuit 17 is arbitrary. In this case, however, the magnification is defined as 1 for the sake of simplifying explanation. That is, the amplifier circuit 17 outputs the voltage having the same voltage value as the sensor-across voltage Vs.

In the current application circuit 19, a resistor 31, a switch 33, a switch 35 and a resistor 37 are connected in series in this order, between a constant power supply voltage VD and a ground line. A connection point between the switch 33 and the switch 35 is connected to the second terminal 7 of the sensor cell 3a. In this example, the switches 33 and 35 are MOSFETs. The switches 33 and 35 may be any other switching elements, such as a bipolar transistor and an insulated gate bipolar transistor. Hereinafter, the switch 35 will be also referred to as the first switch 35, and the switch 33 will be also referred to as the second switch.

The current application circuit 19 includes two operational amplifiers 39 and 41.

The operational amplifier 39 is applied with a voltage of a connection point between the resistor 31 and the second switch 33, and a predetermined voltage Vp. The operational amplifier 41 is applied with a voltage of a connection point between the resistor 37 and the first switch 35, and a predetermined voltage Vm.

When the operational amplifier 41 receives a first switch on command from the control circuit 21, the operational amplifier 41 turns on the switch 35 so that the voltage of the connection point between the resistor 37 and the first switch 35 coincides with the voltage Vm. When the operational amplifier 41 does not receive the first switch on command, the operational amplifier 41 turns off the first switch 35. The first switch on command is, for example, a high-active signal.

Likewise, when the operational amplifier 39 receives a second switch on command from the control circuit 21, the operational amplifier 39 turns on the second switch 33 so that the voltage of the connection point between the resistor 31 and the switch 33 coincides with the voltage Vp. When the operational amplifier 39 does not receive the second switch on command, the operational amplifier 39 turns off the second switch 33. The second switch on command is, for example, a high-active signal.

In this case, a resistance value of the resistor 31 is referred to as a resistance value R31, and a resistance value of the resistor 37 is referred to as a resistance value R37.

When the first switch 35 is turned on according to the first switch on command outputted from the control circuit 21, a current expressed by "Vm/R37" is applied to the sensor cell 3a in a direction from the first terminal 5 to the second terminal 7. Hereinafter, this current, that is, the current flowing in the sensor cell 3a due to the first switch 35 being turned on is referred to as the "current −Iz".

When the second switch 33 is turned on according to the second switch on command outputted from the control circuit 21, a current expressed by "(VD−Vp)/R31" is applied to the sensor cell 3a in a direction from the second terminal 7 to the first terminal 5. Hereinafter, this current, that is, the current flowing in the sensor cell 3a due to the switch 33 being turned on is referred to as the "current +Iz".

The voltage Vm and the voltage Vp are set so that the current −Iz and the current +Iz have the same current value. That is, the current −Iz and the current +Iz are constant currents having the same absolute value but directions thereof are opposite to each other. Hereinafter, the absolute value (current value) of the currents −Iz and +Iz will be referred to as an application current value Iz.

In regard to the directions of the current (application current) applied to the sensor cell 3a, when the direction of the current −Iz is defined as a negative direction, the current −Iz is a negative application current and the current +Iz is a positive application current. In the present embodiment, the current −Iz is an impedance detection current for detecting the impedance Z of the sensor cell 3a. The current −Iz corresponds to a first current. The current +Iz corresponds to a second current that is in the opposite direction to the first current.

The control circuit 21 includes a detection portion 21a, a current application control portion 21b, a control prohibition portion 21c, and registers 27, 28 and 29. The control circuit 21 is, for example, provided by a dedicated IC or a microcomputer separate from the microcomputer 23.

Figure 2:
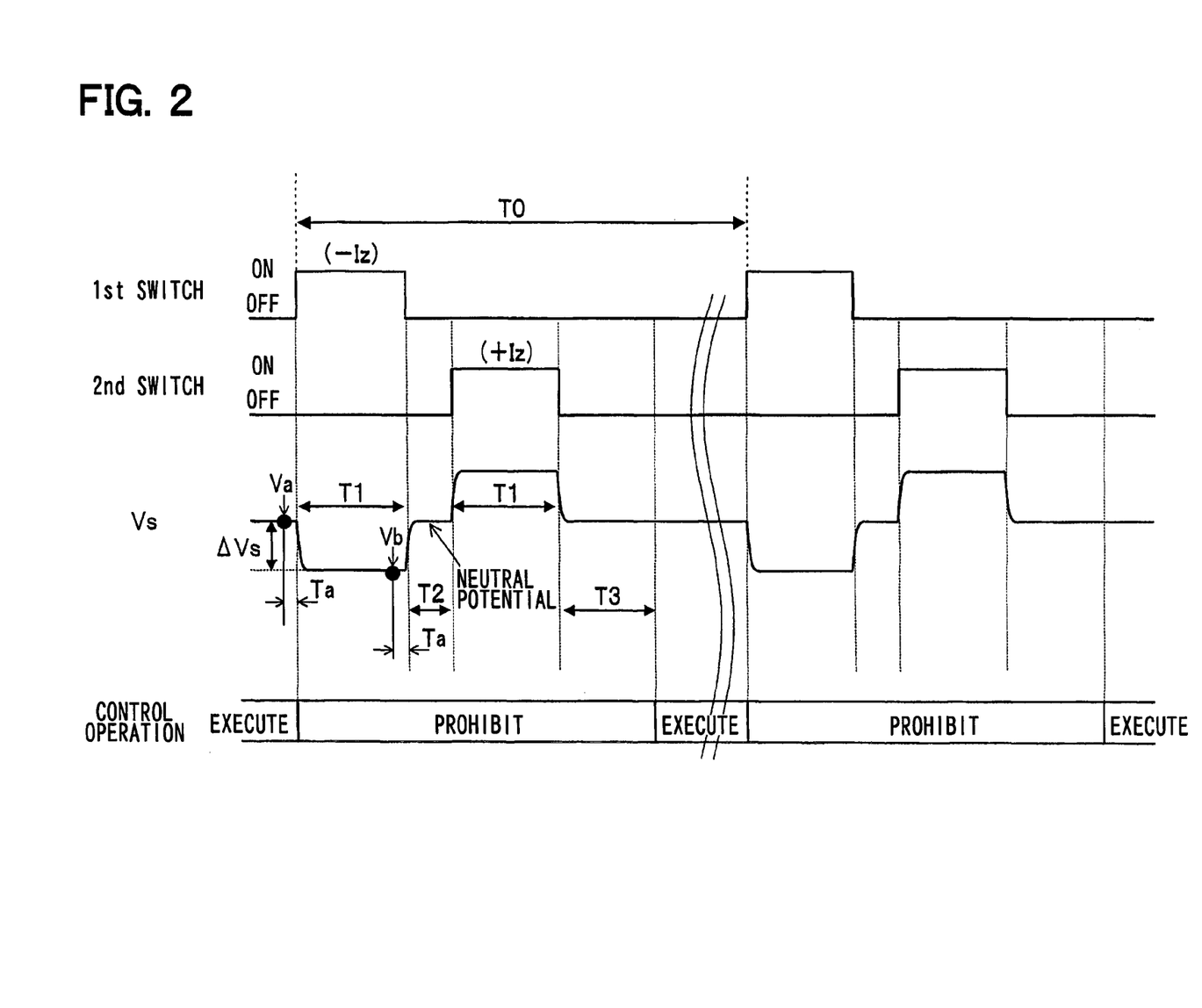
FIG. 2 is a diagram for explaining an operation of the control device according to the first embodiment.

As shown in a first waveform and a second waveform of FIG. 2, the current application control portion 21b of the control circuit 21 turns on the first switch 35 and the second switch 33 in order, for example, every constant period of time T0. The constant period T0 is a period of time for detecting the impedance Z of the sensor cell 3a.

Specifically, the current application control portion 21b makes the first switch on command at a high level only for a period of time T1 stored in the register 27, to thereby turn on the first switch 35 for the period of time T1. When a period of time T2, which is stored in the register 28, elapses after the first switch 35 is turned off, the current application control portion 21b makes the second switch on command at a high level only for the period of time T1, to thereby turn on the second switch 33 for the period of time T1.

Therefore, every constant period of time T0, the current application circuit 19 applies the current −Iz to the sensor cell 3a for the period of time T1 and applies the current +Iz, which has the same value but in the opposite direction to the current −Iz, for the period of time T1 after the period of time T2 elapses since the application of the current −Iz ends. The period of time T1 is for applying the current −Iz and the current +Iz to the sensor cell 3a. Hereinafter, the period of time T1 will be also referred to as a current application time T1. The period of time T2 is a standby time period that begins from the time the application of the current −Iz to the sensor cell 3a ends to the time the application of the current +Iz to the sensor cell 3a begins. Hereinafter, the period of time T2 will be also referred to as a sweep standby time T2.

The current application time T1 and the sweep standby time T2 are, respectively, written into the register 27 and the register 28 of the control circuit 21 by the microcomputer 23. That is, the current application circuit 19 and the current application control portion 21b are configured to change each of the current application time T1 and the sweep standby time T2 according to a command provided from the microcomputer 23. The microcomputer 23 commands the current application time period T1 and the sweep standby time period T2 by writing the respective values into the register 27 and the register 28.

As shown in a third waveform in FIG. 2, the sensor-across voltage Vs changes when the current −Iz and the current +Iz are applied to the sensor cell 3a. In FIG. 2, the sensor-across voltage Vs is indicated as a voltage of the second terminal 7 relative to the voltage of the first terminal 5 as a reference. Therefore, the sensor-across voltage Vs is reduced by the application of the current −Iz (turning on of the first switch 35) and is increased by the application of the current +Iz (turning on of the second switch 33).

The detection portion 21a operates in cooperation with the current application control portion 21b. The detection portion 21a detects a current application prior voltage Va that is the sensor-across voltage Vs immediately before the current −Iz is applied to the sensor cell 3a, and a current application subsequent voltage Vb that is the sensor-across voltage Vs in a period where the current −Iz is being applied. In this example, the current application subsequent voltage Vb is the sensor-across voltage Vs immediately before the application of the current −Iz is ended.

Specifically, the detection portion 21a detects the sensor-across voltage Vs, as the current application prior voltage Va, at a time a predetermined time Ta prior to the time the first switch 35 is turned on from the off state, that is, at a time the predetermined time Ta prior to the time where the current application circuit 19 begins the application of the current −Iz. The detection portion 21a detects the sensor-across voltage Vs, as the current application subsequent voltage Vb, at a time the predetermined time Ta prior to the time where the first switch 35 is turned off from the on state, that is, at a time the predetermined time Ta prior to the time where the current application circuit 19 ends the application of the current −Iz.

The predetermined time Ta is a period of time sufficiently shorter than the current application time T1 in which the first switch 35 is turned on. Therefore, the sensor-across voltage Vs immediately before the application of the current −Iz to the sensor cell 3a is initiated and the sensor-across voltage Vs immediately before the application of the current −Iz is ended can be detected, respectively, as the current application prior voltage Va and the current application subsequent voltage Vb. It is to be noted that the predetermined time Ta is preferably close to zero as much as possible.

Further, the detection portion 21a calculates a difference ΔVs between the current application prior voltage Va and the current application subsequent voltage Vb, that is, an absolute value of the difference between the current application prior voltage Va and the current application subsequent voltage Vb (see the third waveform in FIG. 2). The difference ΔVs is the amount of change of the sensor-across voltage Vs due to the application of the current −Iz to the sensor cell 3a, and is proportional to the impedance Z of the sensor cell 3a and the current −Iz. The detection portion 21a outputs the difference ΔVs calculated to the microcomputer 23.

The microcomputer 23 performs an impedance calculation processing for calculating the impedance Z of the sensor cell 3a, for example, in every constant time period. In the impedance calculating processing, the microcomputer 23 obtains the difference ΔVs from the detection portion 21a, and calculates the impedance Z based on the difference ΔVs and the value of the applied current Iz. Specifically, the impedance Z can be calculated by dividing the difference ΔVs by the value of the applied current Iz (Z=ΔVs/Iz).

The impedance Z has a correlation with the temperature of the sensor cell 3a. Therefore, the microcomputer 23 determines whether the sensor cell 3a is in an active state based on the impedance Z calculated, or controls the electricity to the heater 3b so that the temperature of the sensor cell 3a coincides with a target temperature.

After the current −Iz for detecting the impedance Z is applied to the sensor cell 3a, the current −Iz, which is opposite to the current −Iz is applied to the sensor cell 3a for the same period of time as the application of the current −Iz so as to shorten a normal return time that is a period of time required to return the state of the sensor cell 3a to the normal state for detecting the air fuel ratio, that is, to the state where the sensor current. has a value corresponding to the air fuel ratio.

The microcomputer 23 detects the sensor current based on the output voltage of the amplifier circuit 16, and calculates the air fuel ratio by applying the sensor current detected to a predetermined formula or a data map. That is, the sensor current is converted into the air fuel ratio. The air fuel ratio calculated is used for a feedback control of the air fuel ratio of the internal combustion engine. The processing for detecting the sensor current, the processing for converting the sensor current into the air fuel ratio may be performed by a microcomputer separate from the microcomputer 23.

The control prohibition portion 21c of the control circuit 21 operates in cooperation with the current application control portion 21b. The control prohibition portion 21c prohibits a control operation of the voltage control part 13, that is, an operation to change the application voltage to the sensor cell 3a according to the sensor current.

Specifically, as shown in the fourth item in FIG. 2, the control prohibition portion 21c prohibits the control operation of the voltage control part 13 in a period that begins from the time the first switch 35 is turned on, that is, the time the application of the current −Iz is initiated and ends at a time where a time T3 has elapsed after the second switch 33 was turned off from the on state, that is, after the application of the current +Iz was ended. The time T3 is stored in the register 29. In FIG. 2, the control operation of the voltage control part 13 is indicated by "control operation".

When the current −Iz and the current +Iz are applied to the sensor cell 3a, the sensor current detected by the resistor 11 is not a current according to the air fuel ratio. The sensor cell 3a requires the normal return time for some extent to return to the normal state for detecting the air fuel ratio after the applications of the current −Iz and +Iz to the sensor cell 3a are ended. The sensor current is not the current according to the air fuel ratio until the normal return time elapses.

Therefore, the control prohibition portion 21c prohibits the control operation of the voltage control part 13 during the period indicated as "prohibit" in the fourth item in FIG. 2 so as to restrict the application voltage to the sensor cell 3a from being adjusted to an improper value, thereby to restrict degradation of accuracy of the air fuel detection. In the period of time where the control prohibition portion 21c prohibits the control operation of the voltage control part 13, the microcomputer 23 stops the detection of the sensor current and the calculation of the air fuel ratio.

The time T3 is the period of time to continue the prohibition of the control operation of the voltage control part 13 after the applications of the currents −Iz and +Iz to the sensor cell 3a are ended. The time T3 is set to a period of time longer than the normal return time of the sensor cell 3a. Hereinafter, the time T3 will be also referred to as a prohibition duration time T3.

The prohibition duration time T3 is also written in the register 29 of the control circuit 21 by the microcomputer 23. That is, the control prohibition portion 21c is configured to change the prohibition duration time T3 according to a command provided from the microcomputer 23. The microcomputer 23 writes the value in the register 29 to command the prohibition duration time T3.

As described above, the control circuit 21 is configured to change each of the current application time T1, the sweep standby time T2 and the prohibition duration time T3 according to the command from the microcomputer 23. This is because an optimal value of each of the times T1 to T3 is different depending on the electrical characteristics of the sensor cell 3a as the object to detect the impedance, that is, the type of the air fuel ratio sensor 3.

The period of time from the time the application of the current −Iz to the sensor cell 3a is initiated to the time the sensor-across voltage Vs reaches the value according to the impedance Z is different depending on the electrical characteristic of the sensor cell 3a. Hereinafter, this period of time will also be referred to as the convergence time.

It is preferable that the current application time T1 is longer than the convergence time, but is minimum. This is because, when the current application time T1 is shorter than the convergence time, the application of the current −Iz is ended before the sensor-across voltage Vs reaches the value according to the impedance Z, and thus it is difficult to accurately detect the amount of change of the sensor-across voltage Vs due to the application of the current −Iz, that is, the difference ΔVs, which results in the impedance Z. On the other hand, when the current application time T1 is excessively long, the period of time where the air fuel ratio cannot be detected is long, and thus it not preferable. As described above, in the current sweep period where the currents −Iz and +Iz are applied to the sensor cell 3a in order, the sensor current flowing in the sensor cell 3a does not have the value according to the air fuel ratio. Therefore, the air fuel ratio cannot be detected.

Also, the period of time from the time the application of the current −Iz to the sensor cell 3a is ended to the time that the sensor-across voltage Vs returns to the voltage before the application of the current −Iz is different depending on the electrical characteristics of the sensor cell 3a. Hereinafter, this period of time will be also referred to as a neutral return period, and the voltage same as before the application of the current −Iz will be also referred to as the neutral potential.

It is preferable that the sweep standby time T2 is longer than the neutral return time, but is minimum. This is because, when the sweep standby time T2 is shorter than the neutral return time, the application of the current +Iz to the sensor cell 3a is initiated before the sensor-across voltage Vs returns to the neutral voltage after the application of the current −Iz is ended.

In such a case, an integrated value of the change of the sensor-across voltage Vs due to the application of the current −Iz to the sensor cell 3a and an integrated value of the change of the sensor-across voltage Vs due to the application of the current +Iz to the sensor cell 3a are not equal to each other. The integrated value of the change of the sensor-across voltage Vs due to the application of the current −Iz to the sensor cell 3a corresponds to an integrated value of the change in a downward direction in the third waveform in FIG. 2. The integrated value of the change of the sensor-across voltage Vs due to the application of the current +Iz to the sensor cell 3a corresponds to an integrated value of the change in an upward direction in the third waveform in FIG. 2. As a result, the normal return time of the sensor cell 3a becomes long. On the other hand, even if the sweep standby time T2 is excessively long, the time period in which the air fuel ratio cannot be detected becomes long, and hence it is not preferable.

Further, the normal return time required to return the state of the sensor cell 3a to the normal state for detecting the air fuel ratio after the applications of the currents −Iz and +Iz to the sensor cell 3a are ended is different depending on the electrical characteristics of the sensor cell 3a.

It is preferable that the prohibition duration time T3 is longer than the normal return time of the sensor cell 3a, but is minimum. This is because, when the prohibition duration time T3 is shorter than the normal return time, the control operation of the voltage control part 13 is executed before the sensor cell 3a returns to the normal state, that is, before the sensor current returns to the current according to the air fuel ratio. As a result, the application voltage to the sensor cell 3a is adjusted to an improper value, and thus the accuracy of detection of the air fuel ratio thereafter is degraded. On the other hand, even if the prohibition duration time T3 is excessively long, the period where the air fuel ratio cannot be detected becomes long, and hence it is not preferable.

Figure 3:
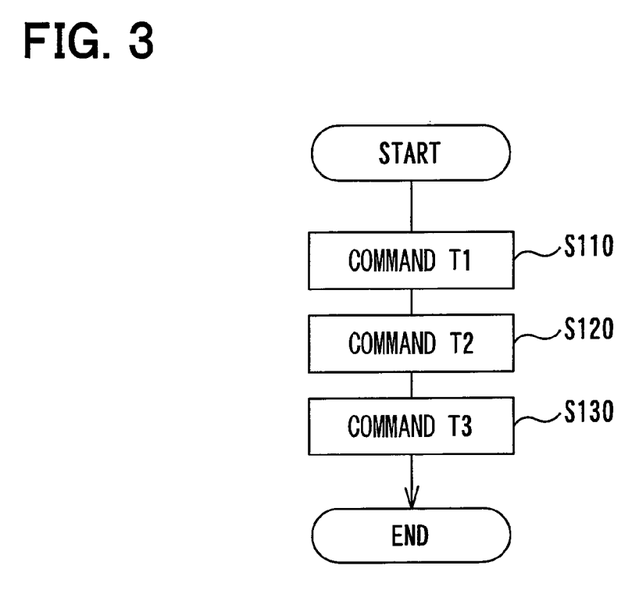
FIG. 3 is a flowchart illustrating a parameter setting processing according to the first embodiment.

Therefore, the microcomputer 23 performs a parameter setting processing shown in FIG. 3, when activated. Through the parameter setting processing shown in FIG. 3, the microcomputer 23 commands the times T1 to T3 suitable for the air fuel ratio sensor 3 connected to the control device 1 to the control circuit 21 (S110 to S130). Specifically, the microcomputer 23 writes the times T1 to T3 to the registers 27 to 29 of the control circuit 21. In this case, the times T1 to T3 correspond to "parameters". As another example, each of the times T1 to T3 (i.e., data of the times T1 to T3) may be transmitted to the control circuit 21 from the microcomputer 23 through a signal line, and each of the times T1 to T3 transmitted may be written in a corresponding one of the registers 27 to 29 by a writing control portion of the control circuit 21.

Figure 4:
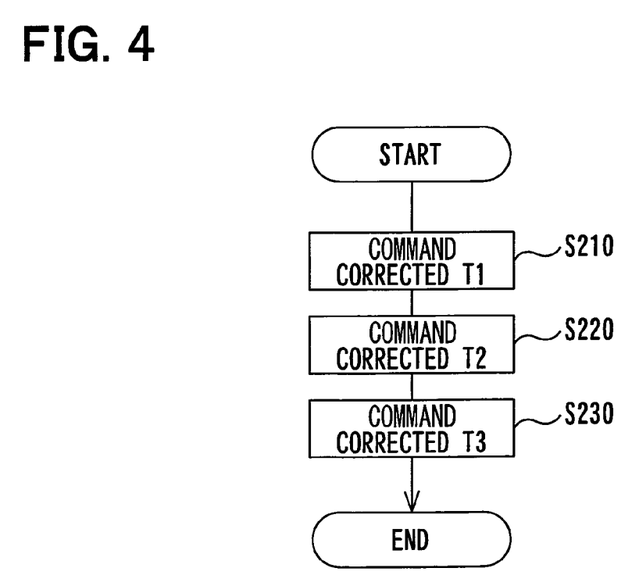
FIG. 4 is a flowchart illustrating a parameter changing processing according to the first embodiment.

The microcomputer 23 performs a parameter changing processing shown in FIG. 4 for every constant period of time. In the following descriptions, initial setting values of the times T1 to T3 are the times T1 to T3 commanded by the microcomputer 23 to the control circuit 21 in the parameter setting processing shown in FIG. 3.

In the parameter changing processing, as shown in FIG. 4, the microcomputer 23 corrects the initial setting value of the time T1, at S210, according to the impedance Z of the sensor cell 3a calculated by the impedance calculation processing described above. The microcomputer 23 commands the time T1 corrected to the control circuit 21. Specifically, the time T1 corrected is overwritten in the register 27 of the control circuit 21.

The impedance Z of the sensor cell 3a varies according to the temperature. The convergence time described above becomes short as the impedance Z reduces. Therefore, at S210, the microcomputer 23 corrects the time T1 to a smaller value as the impedance Z is smaller, for example, and then commands the time T1 corrected to the control circuit 21.

At S220, the microcomputer 23 corrects the initial setting value of the time T2 according to the impedance Z of the sensor cell 3a. Then, the microcomputer 23 commands the time T2 corrected to the control circuit 21. Specifically, the microcomputer 23 overwrites the time T2 corrected to the register 28 of the control circuit 21.

As the impedance Z of the sensor cell 3a is reduced, the neutral return time described above is shortened. Therefore, at S220, the microcomputer 23 corrects the time T2 to a smaller value as the impedance Z is smaller, for example, and then commands the time T2 corrected to the control circuit 21.

At S230, the microcomputer 23 corrects the initial setting value of the time T3 according to the impedance Z of the sensor cell 3a. Then, the microcomputer 23 commands the time T3 corrected to the control circuit 21. Specifically, the microcomputer 23 overwrites the time T3 corrected to the register 29 of the control circuit 21.

As the impedance Z of the sensor cell 3a is reduced, the neutral return time described above is shortened. Therefore, at S230, the microcomputer 23 corrects the time T3 to a smaller value as the impedance Z is smaller, for example, and then commands the time T3 corrected to the control circuit 21. Thereafter, the microcomputer 23 ends the parameter changing processing.

In the control device 1 described above, the current application circuit 19 and the current application control portion 21b of the control circuit 21 are configured to apply the currents −Iz and +Iz to the sensor cell 3a in predetermined order. The current application circuit 19 and the current application control portion 21b are further configured to change the current application time T1 according to the command provided from the external, for example, from the microcomputer 23. Therefore, the current application time T1 can be changed to a suitable value, that is, to a minimum necessary value, according to the air fuel ratio sensor 3 used. As a result, the operation for detecting the impedance Z can be optimized.

The current application circuit 19 and the current application control portion 21b are further configured to change the sweep standby time T2 according to the command provided from the external, for example, from the microcomputer 23. Therefore, the sweep standby time T2 can be changed to a suitable value, that is, to a minimum necessary value, according to the air fuel ratio sensor 3 used.

The control device 1 includes: the voltage control part 13 that changes the application voltage to the sensor cell 3a according to the sensor current; and the control prohibition portion 21c that prohibits the control operation of the voltage control part 13. The control prohibition portion 21c is configured to change the prohibition duration time T3 described above according to the command provided from the external, such as from the microcomputer 23. Therefore, the prohibition duration time T3 can be changed to the suitable value, that is, to a minimum necessary value, according to the air fuel ratio sensor 3 used.

The microcomputer 23 changes (corrects) the command value of each of the times T1 to T3 according to the impedance Z of the sensor cell 3a calculated. Therefore, the times T1 to T3 can be optimized even during the operation of the control device 1.

As the configuration of changing the times T1 to T3, the times T1 to T3 may be changed to any of values that are set in multiple ways, or changed in non-stepwise or continuously.

Second Embodiment

Next, a control device according to a second embodiment of the present disclosure will be described.

Hereinafter, structural elements and processing similar to those of the first embodiment will be designated with the like reference numbers, and descriptions thereof will not be repeated.

Figure 5:
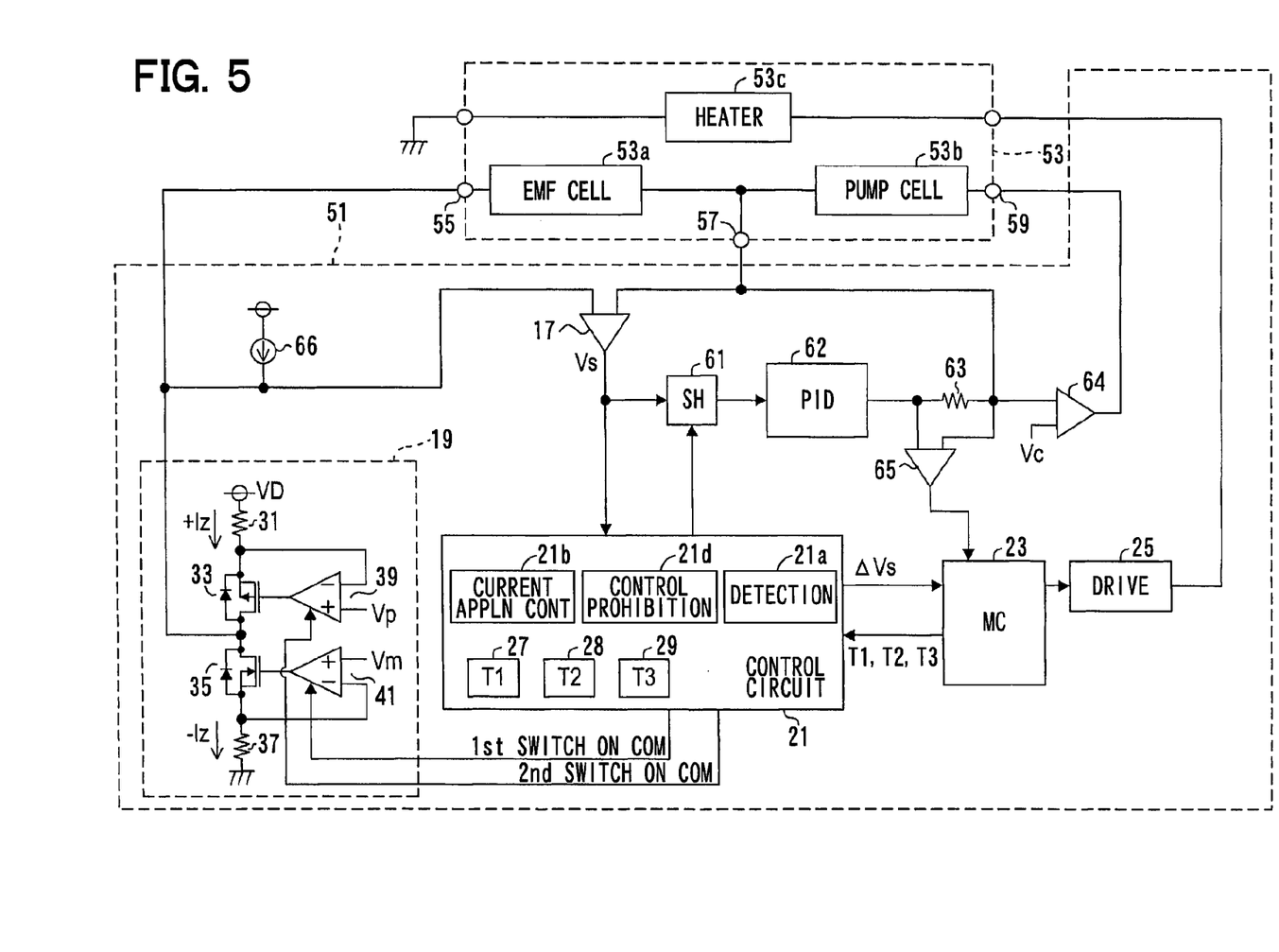
FIG. 5 is a schematic block diagram illustrating a structure of a control device for an impedance detector according to a second embodiment of the present disclosure.

Referring to FIG. 5, a control device 51 of the second embodiment is different from the control device 1 of the first embodiment on the following points (A1) to (A4).

(A1) An air fuel ratio sensor 53 is an oxygen concentration sensor and is connected to the control device 51. The air fuel ratio sensor 53 is a two cell type air fuel ratio sensor having two cells, such as an electromotive force cell 53a and a pump cell 53b. In the air fuel ratio sensor 53, the pump cell 53b is operated such that an output voltage (electromotive force) of the electromotive force cell 53a has a target value. The output voltage of the electromotive force cell 53a is defined according to a difference of oxygen concentration between a diffusion chamber (i.e., gas detection chamber) into which an exhaust gas is introduced and a reference oxygen chamber. An electric current flowing in the pump cell 53b when the pump cell 53b is operated in the above manner is sensed as the sensor current indicating the air fuel ratio. The air fuel sensor 53 further includes a heater 53c. Similarly to the first embodiment, the heater 53c is turned on by the drive circuit 25 of the control device 51 to heat the electromotive force cell 53a and the pump cell 53b.

(A2) The electromotive force cell 53a is the element as an object to detect the impedance. Therefore, a connection point between the switch 33 and the switch 35 in the current application circuit 19 is connected to one terminal 55 of the electromotive force cell 53a. The other terminal 57 of the electromotive force cell 53a is a common terminal with the pump cell 53b. The amplifier circuit 17 outputs the output voltage of the electromotive force cell 53a, that is, a voltage between the terminal 55 and the terminal 57, as the sensor-across voltage Vs. In this example, the terminal 55 is a positive-side terminal of the electromotive force cell 53a, and the terminal 57 is a negative-side terminal of the electromotive force cell 53a and the pump cell 53b. The other terminal 59 of the pump cell 53b is a positive-side terminal of the pump cell 53b.

(A3) The control device 51 does not include the resistor 11, the operational amplifier 12, the voltage control part 13, the buffer circuit 14, the voltage output part 15, and the amplifier circuit 16. Instead, the control device 51 includes a sample hold circuit (SH) 61, a PID circuit 62, a resistor 63, an operational amplifier 64, an amplifier circuit 65, and a constant current circuit 66. The resistor 63 is for detecting the sensor current. The amplifier circuit 65 amplifies and outputs a both-end voltage of the resistor 63. The constant current circuit 66 applies a constant current for generating an electromotive force in the electromotive force cell 53a to the terminal 55.

The sensor-across voltage Vs provided from the amplifier circuit 17, that is, the output voltage of the electromotive force cell 53a is inputted to the PID circuit 62 through the sample hold circuit 61. An output terminal of the PID circuit 62 is connected to the terminal 57 through the resistor 63. The PID circuit 62 performs a PID control that determines an output voltage based on a deviation between an input voltage, which is the sensor-across voltage Vs inputted to the PID circuit 62 through the sample hold circuit 61, and a target value Vt, to thereby change the output voltage so that the input voltage has the target value Vt. The operational amplifier 64 is applied with the voltage of the terminal 57 and a constant voltage Vc (e.g., 2.5 V). The output terminal of the operational amplifier 64 is connected to the terminal 59. The operational amplifier 64 outputs a voltage to the terminal 59 so that the terminal 57 has the voltage Vc.

In such a configuration, the PID circuit 62 adjusts a pump cell current that flows in the pump cell 53b according to the sensor-across voltage Vs as the output voltage of the electromotive force cell 53a so that the sensor-across voltage Vs has the target value Vt. The pump cell current flows in the resistor 63 as the sensor current indicating the air fuel ratio. The amplifier circuit 65 outputs a voltage proportional to the sensor current. Further, the microcomputer 23 detects the sensor current based on the output voltage of the amplifier circuit 65. The microcomputer 23 calculates the air fuel ratio by applying the sensor current detected to a predetermined formula or a data map.

When the control circuit 21 outputs a hold command signal, the sample hold circuit 61 is in a hold mode to hold the sensor-across voltage Vs at a time where the hold command signal is outputted and to continue to output the sensor-across voltage Vs held to the PID circuit 62. When the control circuit 21 stops to output the hold command signal, the sample hold circuit 61 turns to a normal mode to output the sensor-across voltage Vs outputted from the amplifier circuit 17 to the PID circuit 62.

(A4) The control circuit 21 includes a control prohibition portion 21d, in place of the control prohibition portion 21c of the first embodiment.

The control prohibition portion 21d is operated in cooperation with the current application control portion 21b. The control prohibition portion 21d prohibits the control operation of the PID circuit 62 in cooperation with the current application control portion 21b. In particular, the control operation of the PID circuit 62 is an operation to adjust the current flowing in the pump cell 53b according to the output voltage of the electromotive force cell 53a. In the present embodiment, the control prohibition portion 21d prohibits the control operation of the PID circuit 62 by outputting the hold command signal described above to the sample hold circuit 61. When the sample hold circuit 61 turns to the hold mode, the voltage inputted to the PID circuit 62 does not change. Therefore, the control operation of the PID circuit 62 is prohibited.

Similarly to the control prohibition portion 21c of the first embodiment, the control prohibition portion 21d outputs the hold command signal to the sample hold circuit 61 to prohibit the control operation of the PID circuit 62 (see the fourth item in FIG. 2), in the period from the time the first switch 35 is turned on to the time the time T3 stored in the register 29 elapses after the second switch 33 is turned off from the on state.

When the electromotive force cell 53a is applied with the currents −Iz and +Iz, the output voltage of the electromotive force cell 53a, that is, the sensor-across voltage Vs changes irrespective of the air fuel ratio. The normal return time for some extent is necessary to return the electromotive force cell 53a to the normal state for the detection of the air fuel ratio after the application of the currents −Iz and +Iz to the electromotive force cell 53a is ended, that is, to return the output voltage of the electromotive force cell 53a to the normal value corresponding to the proper oxygen concentration difference. Therefore, the control prohibition portion 21*d* prohibits the control operation of the PID circuit 62 in the period indicated as "prohibition" in the fourth item of FIG. 2 to restrict the current (sensor current) flowing in the pump cell 53*b* from being adjusted to an improper value. Accordingly, the degradation of the detection accuracy of the air fuel ratio can be reduced.

In the second embodiment, the time T3 is the period of time to keep the prohibition of the control operation of the PID circuit 62 after the application of the currents −Iz and +Iz to the sensor cell 3*a* is ended. Also in the second embodiment, the time T3 is also referred to as the prohibition duration time T3.

The normal return time necessary to return the electromotive force cell 53*a* to the normal state for the detection of the air fuel ratio after the completion of the application of the currents −Iz and +Iz is different depending on the electrical characteristics of the electromotive force cell 53*a*. It is preferable that the prohibition duration time T3 is longer than the normal return time of the electromotive force cell 53*a*, but is minimum.

Also in the second embodiment, therefore, the prohibition duration time T3 is written in the register 29 by the microcomputer 23. That is, the control prohibition portion 21*d* is configured to change the prohibition duration time T3 according to the command provided from the microcomputer 23. The microcomputer 23 writes the value to the register 29, thereby to command the prohibition duration time T3.

The other structures and processing of the control device 51 of the second embodiment are similar to those of the control device 1 of the first embodiment. In the parameter changing processing shown in FIG. 4, the microcomputer 23 corrects the initial setting values of the times T1 to T3 according to the impedance Z of the electromotive force cell 53*a*.

Also in the control device 51 of the second embodiment, in regard to the current application time T1, the sweep standby time T2 and the prohibition duration time T3, the advantageous effects similar to those achieved by the control device 1 of the first embodiment will be achieved. In the second embodiment, it is not always necessary that the microcomputer 23 stops the detection of the sensor current and the calculation of the air fuel ratio in the period where the control prohibition portion 21*d* prohibits the control operation of the PID circuit 62. However, the microcomputer 23 may stop the detection of the sensor current and the calculation of the air fuel ratio in the period. As another example, the control prohibition portion 21*d* may be configured to hold the output voltage of the PID circuit 62 for prohibiting the control operation of the PID circuit 62.

Third Embodiment

Figure 6:
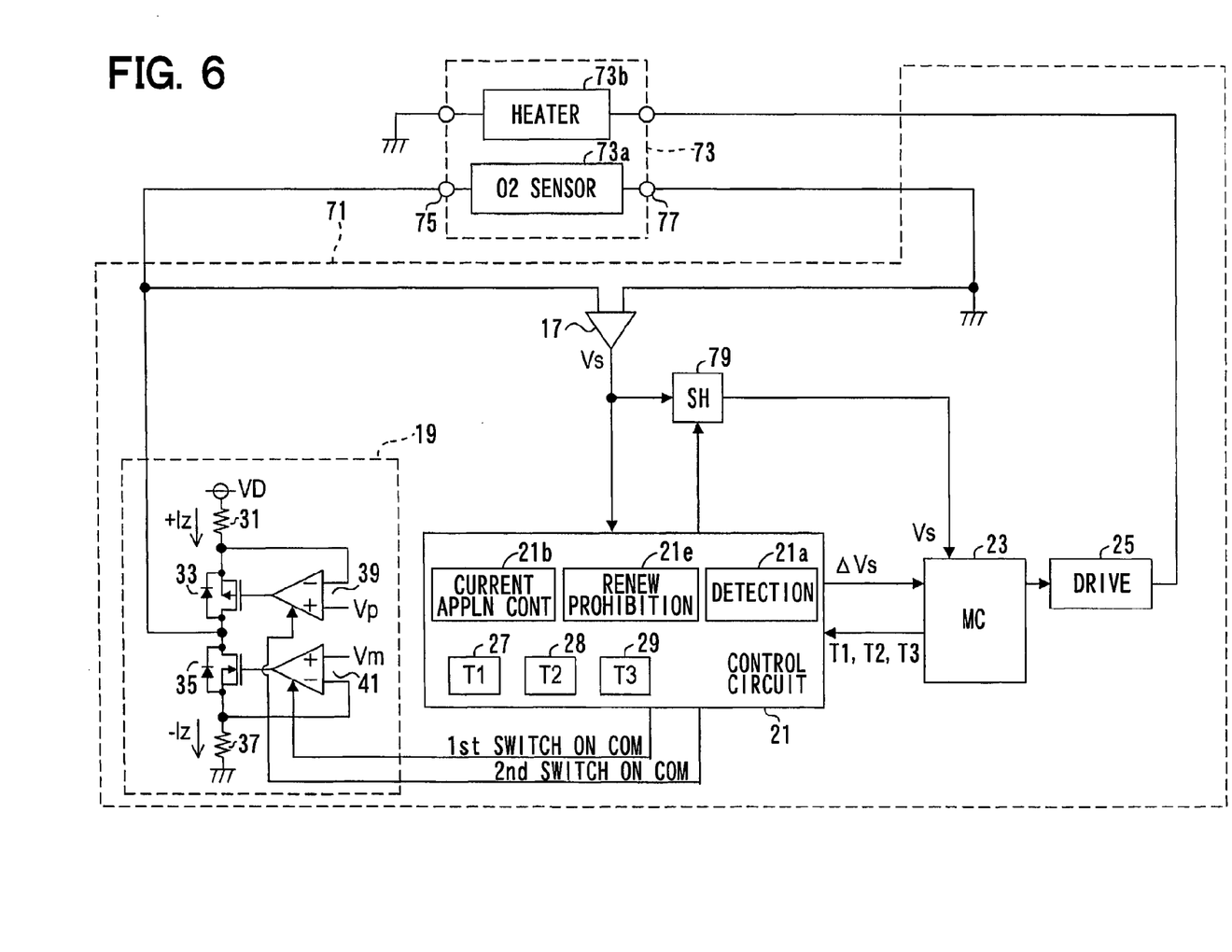
FIG. 6 is a schematic block diagram illustrating a structure of a control device for an impedance detector according to a third embodiment of the present disclosure.

A control device 71 of a third embodiment shown in FIG. 6 is different from the control device 1 of the first embodiment on the following points (B1) to (B4).

(B1) As the oxygen concentration sensor, an O2 sensor 73 is connected to the control device 71. The O2 sensor 73 includes an element 73*a* and a heater 73*b*. The element 73*a* has a characteristic where the output voltage rapidly changes at a predetermined air fuel ratio (e.g., theoretical air fuel ratio), and will be hereinafter referred to as the O2 sensor element 73*a*. Similarly to the first embodiment, the heater 73*b* is turned on by the drive circuit 25 of the control device 71, and heats the O2 sensor element 73*a*.

(B2) The O2 sensor element 73*a* is the element as an object to detect the impedance. The connection point between the switch 33 and the switch 35 of the current application circuit 19 is connected to one terminal 75 of the O2 sensor element 73*a*. The other terminal 77 of the O2 sensor element 73*a* is connected to a ground line of a reference potential. The amplifier circuit 17 outputs an output voltage of the O2 sensor element 73*a*, that is, a voltage between the terminal 75 and the terminal 77 as the sensor-across voltage Vs.

(B3) The control device 71 does not include the resistor 11, the operational amplifier 12, the voltage control part 13, the buffer circuit 14, the voltage output part 15 and the amplifier circuit 16. Instead, the control circuit 21 includes a sample hold circuit (SH) 79 that outputs the sensor-across voltage Vs provided from the amplifier circuit 17 to the microcomputer 23.

When the control circuit 21 outputs a hold command signal, the sample hold circuit 79 turns to a hold mode to hold the sensor-across voltage Vs at a time the hold command signal is outputted and to continue to output the sensor-across voltage Vs held to the microcomputer 23. When the control circuit 21 stops to output the hold command signal, the sample hold circuit 79 turns to a normal mode to output the sensor-across voltage Vs outputted from the amplifier circuit 17 to the microcomputer 23.

The microcomputer 23 performs an air fuel ratio determination to determine whether the air fuel ratio is lean or rich based on the sensor-across voltage Vs provided from the sample hold circuit 79. For example, when the sensor-across voltage Vs inputted to the microcomputer 23 is lower than a threshold, the microcomputer 23 determines that the air fuel ratio is lean. When the sensor-across voltage Vs is equal to or higher than the threshold, the microcomputer 23 determines that the air fuel ratio is rich.

(B4) The control circuit 21 includes a renewing prohibition portion 21*e*, in place of the control prohibition portion 21*c*.

The renewing prohibition portion 21*e* is operated in cooperation with the current application control portion 21*b*, and prohibits renewing of the sensor-across voltage Vs inputted to the microcomputer 23. In the present embodiment, the renewing prohibition portion 21*e* prohibits the renewing of the sensor-across voltage Vs inputted to the microcomputer 23 by outputting the hold command signal to the sample hold circuit 79 and setting the sample hold circuit 79 to the hold mode.

Similarly to the control prohibition portion 21*c* of the first embodiment, the renewing prohibition portion 21*e* outputs the hold command signal to the sample hold circuit 79 to prohibit the sensor-across voltage Vs inputted to the microcomputer 23 from being renewed, in a period from the time the first switch 35 is turned on to the time the time T3 stored in the register 29 has elapsed after the second switch 33 was turned off from the on state (see the fourth item in FIG. 2).

When the O2 sensor element 73*a* is applied with the currents −Iz and +Iz, the output voltage of the O2 sensor element 73*a*, that is, the sensor-across voltage Vs changes irrespective of an actual air fuel ratio. The normal return time for some extent is necessary to return the O2 sensor element 73*a* to the normal state for the detection of the air fuel ratio after the application of the currents −Iz and +Iz to the O2 sensor element 73*a* is ended, that is, to return the output voltage of the O2 sensor element 73*a* to the normal value corresponding to the air fuel ratio. Therefore, the renewing prohibition portion 21*e* prohibits the renewing of the sensor-across voltage Vs inputted to the microcomputer 23 in the period indicated as "prohibition" in the fourth item of FIG. 2 to restrict erroneous determination of the microcomputer 23 whether the air fuel ratio is lean or rich.

In the third embodiment, the time T3 is a period of time to keep the prohibition of the renewing of the sensor-across voltage Vs inputted to the microcomputer 23 even after the application of the currents −Iz and +Iz to the O2 sensor element 73a is ended. Also in the third embodiment, the time T3 is also referred to as the prohibition duration time T3.

The normal return time necessary to return the O2 sensor element 73a to the normal state for the detection of the air fuel ratio after the completion of the application of the currents −Iz and +Iz is different depending on the electrical characteristics of the O2 sensor element 73a. It is preferable that the prohibition duration time T3 is longer than the normal return time of the O2 sensor element 73a, but is minimum.

Also in the third embodiment, therefore, the prohibition duration time T3 is written in the register 29 by the microcomputer 23. That is, the renewing prohibition portion 21e is configured to change the prohibition duration time T3 according to the command provided from the microcomputer 23. The microcomputer 23 writes the value to the register 29, thereby to command the prohibition duration time T3.

The other structures and processing of the control device 71 of the third embodiment are similar to those of the control device 1 of the first embodiment. In the parameter changing processing shown in FIG. 4, the microcomputer 23 corrects the initial setting values of the times T1 to T3 according to the impedance Z of the O2 sensor element 73a.

Also in the control device 71 of the second embodiment, in regard to the current application time T1, the sweep standby time T2 and the prohibition duration time T3, the advantageous effects similar to those achieved by the control device 1 of the first embodiment will be achieved. In the third embodiment, it is not always necessary that the microcomputer 23 stops the processing for determining whether the air fuel ratio is rich or lean in the period where the renewing prohibition portion 21e prohibits the renewing of the sensor-across voltage Vs inputted to the microcomputer 23. However, the microcomputer 23 may stop the processing for determining whether the air fuel ratio is rich or lean in the period.

The embodiments of the present disclosure are described hereinabove. However, the present disclosure is not limited to the embodiments described above, but may be modified in various other ways. Moreover, the above-mentioned numerical values are examples, and other values may be sufficient.

For example, in the control device 1 of the first embodiment, the times T1 to T3 may be commanded to the control circuit 21 (the current application control portion 21b and the control prohibition portion 21c) by a device other than the microcomputer 23. For example, it may be configured such that a high level voltage or a low level voltage is applied to each of a plurality of time setting terminals of the control circuit 21 through jumper wires, and each of the times T1 to T3 of the registers 27 to 29 may be set to any one of the plurality of values according to combinations of the voltages applied to the time setting terminals.

For example, in the control device 1 of the first embodiment, the current −Iz and the current +Iz are applied in order, that is, one after the other. In the example described above, the current +Iz is applied after the current −Iz is applied. As another example, the current −Iz and the current +Iz may be applied to the sensor cell 3a in order opposite to the order described above, and the current +Iz may be used as the current for detecting the impedance.

For example, in the control device 1 of the first embodiment, the detection portion 21a of the control circuit 21 may also calculate the impedance Z of the sensor cell 3a, and output the impedance Z calculated to the microcomputer 23. In such a case, the microcomputer 23 uses the value of the impedance Z obtained from the detection portion 21a in the parameter changing processing shown in FIG. 4.

The above-described modifications to the first embodiment may also be similarly applied to the control devices 51 and 71 of the second and third embodiments.

For example, the air fuel ratio sensors 3 and 53 and the O2 sensor 73 may not have the heaters 3b, 53c, and 73b. As another example, the heaters 3b, 53c, and 73b may be provided separately from the air fuel ratio sensors 3 and 53 and the O2 sensor 73.

In the embodiments described above, the function of one structural element may be separated into plural structural elements, or the functions of the plural structural elements may be combined into one structural element. For example, at least a part of the structures of the embodiments described above may be replaced with a known structure having the similar function. For example, a part of the structure of the embodiments described above may be eliminated as long as the object can be achieved. For example, a part of the structures of the embodiment described above may be added to another embodiment described above or replaced with the structure of another embodiment described above. In addition to the control device for detecting the impedance of the element described above, the present disclosure may be implemented in various forms such as a system including the control devices described above as a structural element, a program including commands to execute the control device by a computer, a non-transitory computer readable storage medium storing the program, a method for detecting the impedance of the element, and the like.

It is noted that the flowchart or the processing of the flowchart in the present disclosure includes sections (also referred to as steps), each of which is represented, for instance, as S100. Further, each section can be divided into several sub-sections while several sections can be combined into a single section. Furthermore, each of thus configured sections can be also referred to as a circuit, device, module, portion, or means.

While only the selected exemplary embodiment and examples have been chosen to illustrate the present disclosure, it will be apparent to those skilled in the art from this disclosure that various changes and modifications can be made therein without departing from the scope of the disclosure as defined in the appended claims. Furthermore, the foregoing description of the exemplary embodiment and examples according to the present disclosure is provided for illustration only, and not for the purpose of limiting the disclosure as defined by the appended claims and their equivalents.

What is claimed is:

1. An impedance detector for detecting an impedance of an element of an oxygen concentration sensor, the impedance detector comprising:
   a current application portion applying a first current and a second current, directions of which are opposite to each other, to the element of the oxygen concentration sensor in order;
   a detection portion detecting a difference between a current application prior voltage and a current application subsequent voltage, the current application prior voltage being a voltage between both of ends of the element before being applied with the first current, the current application subsequent voltage being a voltage between both of the ends of the element when being applied with the first current; and an impedance calculation portion calculating an impedance of the element based on the difference detected by the detection portion and a value of the first current, wherein the current application portion is configured to change a current application time, which is a period of time to apply the first current and the second current, according to a storage value for the current application time stored in an application time storage portion, and the impedance detector further comprises an application time set portion storing the storage value for the current application time in the application time storage portion.

2. The impedance detector according to claim 1, further comprising:

an application time control portion changing the storage value for the current application time according to the impedance calculated by the impedance calculation portion.

3. The impedance detector according to claim 1, wherein the current application portion is configured to change a sweep standby time, which is a period of time from a time application of the first current is ended to a time application of the second current is initiated, according to a storage value for the sweep standby time stored in a standby time storage portion, and the impedance detector further comprises a standby time set portion storing the storage value for the sweep standby time in the standby time storage portion.

4. The impedance detector according to claim 3, further comprising:

a standby time control portion changing the storage value for the sweep standby time according to the impedance of the element calculated by the impedance calculation portion.

5. The impedance detector according to claim 1, wherein the oxygen concentration sensor is a two cell type air fuel ratio sensor having an electromotive force cell and a pump cell, and the element is the electromotive force cell, the impedance detector further comprising:

a current control portion adjusting a current flowing in the pump cell so that an output voltage of the electromotive force cell has a target value;

an air fuel ratio calculation portion calculating an air fuel ratio based on the current flowing in the pump cell; and a current control prohibition portion prohibiting the current control portion from adjusting the current flowing in the pump cell in a period of time from a time the current application portion initiates application of the first current to a time a predetermined prohibition duration time has elapsed after the current application portion ended application of the second current, wherein the current control prohibition portion is configured to change the prohibition duration time according to a storage value for the prohibition duration time stored in a prohibition duration time storage portion, and the impedance detector further comprising:

a prohibition duration time set portion storing the storage value for the prohibition duration time in the prohibition duration time storage portion.

6. The impedance detector according to claim 5, further comprising:

a prohibition duration time control portion changing the storage value for the prohibition duration time according to the impedance of the element calculated by the impedance calculation portion.

7. An impedance detector for detecting an impedance of an element of an oxygen concentration sensor, the impedance detector comprising:

a current application portion applying a first current and a second current, directions of which are opposite to each other, to the element of the oxygen concentration sensor in order;

a detection portion detecting a difference between a current application prior voltage and a current application subsequent voltage, the current application prior voltage being a voltage between both of ends of the element before being applied with the first current, the current application subsequent voltage being a voltage between both of the ends of the element when being applied with the first current; and an impedance calculation portion calculating an impedance of the element based on the difference detected by the detection portion and a value of the first current, wherein:

the current application portion is configured to change a current application time, which is a period of time to apply the first current and the second current, according to a command provided to the current application portion, the oxygen concentration sensor is a one cell type air fuel ratio sensor having one cell through which a sensor current according to an air fuel ratio flows in a state of being applied with a voltage, the element is the one cell, the impedance detector further comprises:

an air fuel ratio calculation portion calculating an air fuel ratio based on the sensor current;

a voltage control portion changing the voltage applied to the one cell according to the sensor current; and a voltage control prohibition portion prohibiting the voltage control portion from changing the voltage applied to the one cell in a period of time from a time the current application portion initiates application of the first current to a time a predetermined prohibition duration time has elapsed after the current application portion ended application of the second current, and the voltage control prohibition portion is configured to change the prohibition duration time according to a command provided to the voltage control prohibition portion.

8. The impedance detector according to claim 7, further comprising:

a prohibition duration time control portion changing the command for changing the prohibition duration time according to the impedance of the element calculated by the impedance calculation portion.

9. An impedance detector for detecting an impedance of an element of an oxygen concentration sensor, the impedance detector comprising:

a current application portion applying a first current and a second current, directions of which are opposite to each other, to the element of the oxygen concentration sensor in order;

a detection portion detecting a difference between a current application prior voltage and a current application subsequent voltage, the current application prior voltage being a voltage between both of ends of the element before being applied with the first current, the current application subsequent voltage being a voltage between both of the ends of the element when being applied with the first current; and an impedance calculation portion calculating an impedance of the element based on the difference detected by the detection portion and a value of the first current, wherein:

the current application portion is configured to change a current application time, which is a period of time to apply the first current and the second current, according to a command provided to the current application portion, the oxygen concentration sensor is an O2 sensor, the element is included in the O2 sensor, the impedance detector further comprises:

a determination portion receiving an output voltage of the O2 sensor and determining whether an air fuel ratio is lean or rich based on the output voltage of the O2 sensor; and a renewing prohibition portion prohibiting the output voltage received by the determination portion from being renewed in a period of time from a time the current application portion initiates application of the first current to a time a predetermined prohibition duration time has elapsed after the current application portion ended application of the second current, and the renewing prohibition portion is configured to change the prohibition duration time according to a command provided to the renewing prohibition portion.

10. The impedance detector according to claim 9, further comprising a prohibition duration time control portion changing the command for changing the prohibition duration time according to the impedance of the element calculated by the impedance calculation portion.

11. The impedance detector according to claim 1, wherein the detection portion detects the voltage between both of the ends of the element at a time a predetermined time before application of the first current is initiated, as the current application prior voltage, and the detection portion detects the voltage between both of the ends of the element at a time a predetermined time before the application of the first current is ended, as the current application subsequent voltage.

* * * * *